US009782355B2

(12) United States Patent
Casanova Yepes et al.

(10) Patent No.: US 9,782,355 B2
(45) Date of Patent: Oct. 10, 2017

(54) CONTINUOUS METHOD FOR PRODUCING NANOPARTICLES AND NANOPARTICLES OBTAINED BY MEANS OF SAID METHOD

(75) Inventors: Herley Casanova Yepes, Medellin (CO); Lina Paola Higuita Gonzales, Medellin (CO)

(73) Assignee: UNIVERSIDAD DE ANTIOQUIA, Medellin (CO)

( * ) Notice: Subject to any disclaimer, the term of this patent is extended or adjusted under 35 U.S.C. 154(b) by 0 days.

(21) Appl. No.: 14/111,909

(22) PCT Filed: Apr. 13, 2012

(86) PCT No.: PCT/IB2012/051850
§ 371 (c)(1),
(2), (4) Date: Nov. 21, 2013

(87) PCT Pub. No.: WO2012/140626
PCT Pub. Date: Oct. 18, 2012

(65) Prior Publication Data
US 2014/0099377 A1    Apr. 10, 2014

(30) Foreign Application Priority Data

Apr. 15, 2011    (CO) .................................. 11-047523

(51) Int. Cl.
| A61K 9/16 | (2006.01) |
| A61K 9/48 | (2006.01) |
| A61K 9/51 | (2006.01) |
| B82Y 30/00 | (2011.01) |
| B82Y 40/00 | (2011.01) |
| A61K 31/353 | (2006.01) |
| A23P 10/30 | (2016.01) |

(52) U.S. Cl.
CPC ............ *A61K 9/4816* (2013.01); *A23P 10/30* (2016.08); *A61K 9/5115* (2013.01); *A61K 9/5192* (2013.01); *A61K 31/353* (2013.01); *B82Y 30/00* (2013.01); *B82Y 40/00* (2013.01); *A61K 9/5169* (2013.01)

(58) Field of Classification Search
USPC ........................................................ 424/490
See application file for complete search history.

(56) References Cited

U.S. PATENT DOCUMENTS

2010/0086601 A1*  4/2010  McDonough et al. ....... 424/489

FOREIGN PATENT DOCUMENTS

WO    WO2005084637    *   9/2005
WO    WO2007062723    *   4/2010

OTHER PUBLICATIONS

Burgaud (International Journal of Food Science and Technology (1990) 25, 39-46).*
Fu et al., "Why to synthesize vaterite polymorph of calcium carbonate on the cellulose matrix via sonochemistry process?", Ultrasonics Sonochemistry, 20, 1188-1193, 2013.
Xiang et al., "Controllable synthesis of calcium carbonate polymorphs at different temperatures", Powder Technology 189, 64-69, 2009.
Peukert et al.,"Control of aggregation in production and handling of nanoparticles", Chemical Engineering and Processing, 44, 245-252, 2005.
Casanova and Higuita, "Synthesis of calcium carbonate nanoparticles by reactive precipitation using a high pressure jet homogenizer", Chem. Eng. Journal, 175, 569-578, 2011.

* cited by examiner

*Primary Examiner* — Devang Thakor
(74) *Attorney, Agent, or Firm* — Drinker Biddle & Reath LLP

(57) ABSTRACT

The invention relates to a continuous method for producing inorganic or organic nanoparticles having multiple nuclei functionalised with proteins, using a T-type reactor that operates at high pressure, the primary particles that form the nuclei of the nanoparticles being smaller than 10 nm and said primary particles being immersed in a proteinaceous matrix that forms the nanoparticle in sizes of between 30 nm and 500 nm. The invention also relates to the nanoparticles produced by means of said method.

10 Claims, 4 Drawing Sheets

CONTINUOUS METHOD FOR PRODUCING NANOPARTICLES AND NANOPARTICLES OBTAINED BY MEANS OF SAID METHOD

CROSS-REFERENCE TO RELATED APPLICATIONS

This application is a 371 of PCT/IB2012/051850 filed Apr. 13, 2012, which in turn claims the priority of CO 11-047523 filed Apr. 15, 2011, the priority of both applications is hereby claimed and both applications are incorporated by reference herein.

TECHNICAL FIELD

The invention relates to a continuous process for nanoparticles production, whereby it is possible to incorporate chemical, or biological active ingredients within said nanoparticles. During the invention process, the active ingredients are encapsulated or associated with nanoparticles structure to increase protection to environmental conditions, ease of transport, or enhance the controlled release of ingredients in pharmaceutical, chemical, biotechnological and food applications.

BACKGROUND OF THE INVENTION

The organic or inorganic nanoparticles generation can be achieved by two types of techniques, the first one is the milling of solid material to reduce its size to nanometer level and the second one is based on the synthesis starting from precursor salts. Synthesis methods are usually preferred in the preparation of nanoparticles suspensions for industrial applications requiring particle sizes below 500 nm, among which are sonochemistry synthesis, phase separation, microemulsion precipitation and coprecipitation of precursor salts produced by batch or continuous process.

WO2008070538 discloses a process for preparing nanoparticles with encapsulated oil employing "amphiphilic entities", i.e. chemical compounds that have a portion of their structure of hydrophilic nature and the other part of hydrophobic nature. Typically employed amphiphilic entities in said references are natural or synthetic macromolecules which allow emulsifying oil or generating phase separation to encapsulate the oil. The process of this application is done with high-shear or high pressure equipment to achieve the formation of oil nanoparticles with sizes near 100 nm. The nanoparticles producing process to high pressure of WO 2008070538 is applicable only to insoluble liquid compounds and does not apply to water insoluble solid nanoparticles formation.

WO 2007062723 and EP 1792543 disclose a process for preparing a fortified foodstuff with calcium and magnesium nanoparticles respectively, which are stabilized by a biopolymer. The nanoparticles reported in these documents are prepared by homogeneous or heterogeneous precipitation of precursor salts batch and vigorous mixing application. Synthesized nanoparticles have particle sizes between 5 nm and 1000 nm and are stabilized by biopolymers that avoid interaction with other components of the food matrix.

Moreover, U.S. Patent 20100086601 discloses the formation of calcium phosphate nanoparticles generated from the use of polycations or polyanions on the nanoparticle surface using a batch mixing method.

Another paper in this field is WO 2005084637, directed to the method for the production and therapeutic use of calcium phosphate nanoparticles stabilized with surfactants such as bile acid by a batch process through the mixture of precursor salts.

Producing processes of stabilized inorganic nanoparticles with biopolymers, polycations, polyanions or bile acids reported in WO 2007062723, EP 1792543, U.S. 20100086601 and WO 2005084637, are processes by batches made at atmospheric pressure with production efficiencies and, amounts of synthesized material the order of 0.1%, which are inferior to those obtainable at high pressure continuous process whose efficiency becomes the order of 3%.

WO 2007000193 discloses a method for producing isoflavonoids nanoparticles by using a high pressure homogenizer operating at pressures exceeding 50 MPa, thereby generating nano-particles with sizes above 50 nm, which are stabilized with polysaccharides and proteins. The process starting from solid isoflavonoids, which are reduced in size by grinding by high pressure homogenization. This process does not use organic or inorganic precursor salts for generating nanoparticles and not performed on a T-type mixer that operates under high pressure.

WO 1998014174 discloses the nanoparticles formation of compounds with pharmaceutical activity, made by preparing oil-water emulsions of active compounds using a high pressure homogenizer.

After emulsion processing, nanoparticles are generated by evaporation of the emulsion organic phase. This process does not use organic or inorganic precursor salts to generate nanoparticles on a T-type mixer working at high pressure. Further, it presents the disadvantage that solvent evaporation for generation of the nanoparticle may leave solvent residues not fit for food or drug applications.

WO 2008062429 discloses nanoparticles production for releasing active compounds preferably obtained by the sol-gel method; other processing alternatives include high pressure homogenization, bead mill grinding and precipitation. The production method disclosed in this application use as nanoparticles precursors, oxides or alkoxides to generate initially precursor suspensions, which are then subjected to polycondensation processes. In this type of process are not employed precursor salts of insoluble compounds as starting materials for nanoparticles synthesis and homogenization process is employed for the initial dispersion of materials and not to generate nanoparticles.

Finally, U.S. Patent 20060292056 discloses an equipment and a method for producing inorganic nanoparticles by mixing at least two reactants, one of which is sprayed in the form of droplets through a high pressure nozzle. The process is continuous, generates dust particles over 20 microns, composed of aggregated inorganic nanoparticles, whereby loses special properties associated with nanoparticles.

Accordingly, there is a need in the art for a continuous production process capable of preparing, at elevated pressure, a high concentration of uniformly sized nanoparticles stabilized with proteins or polysaccharides in suspension, without the occurrence of nanoparticles aggregation phenomenon, even after one month from their preparation.

BRIEF DESCRIPTION OF THE INVENTION

The object of the present invention is to develop a continuous process for the production of multi-core, organic or inorganic non-aggregated nanoparticles embedded in a protein matrix containing between 50% and 95% solid material (organic or inorganic), stable to sedimentation, to aggregation and with particle sizes between 30 nm and 500 nm.

The process relies on the use of proteins with dispersant, stabilizing and functionalizing capabilities, which form the nanoparticle matrix in which are embedded the primary particles of the organic or inorganic material with sizes below 10 nm, that is between 0.1 nm to 1.0 nm. To accomplish the process of nanoparticles makes use of water soluble, precursor salts, reacting in high flow conditions within a high pressure T-type reactor.

DESCRIPTION OF THE FIGURES

FIG. 3 data indicate a cumulative weight loss of 35% to subject the sample to a temperature of 475° C. Thus, 65% of the nanoparticle is composed of calcium carbonate.

DETAILED DESCRIPTION OF THE INVENTION

Figure 1:
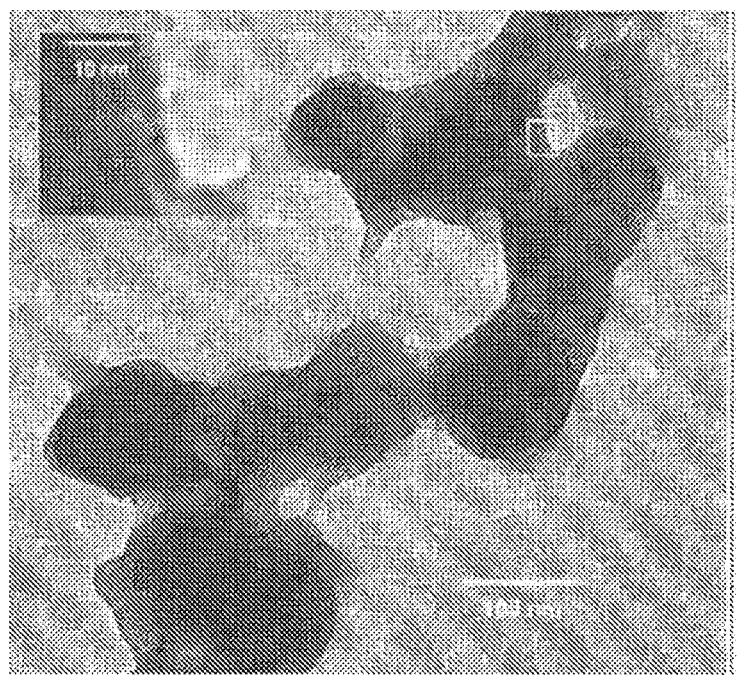
FIG. 1 shows a transmission electron micrograph of calcium carbonate nanoparticles produced by the process of the present invention.
Figure 2:
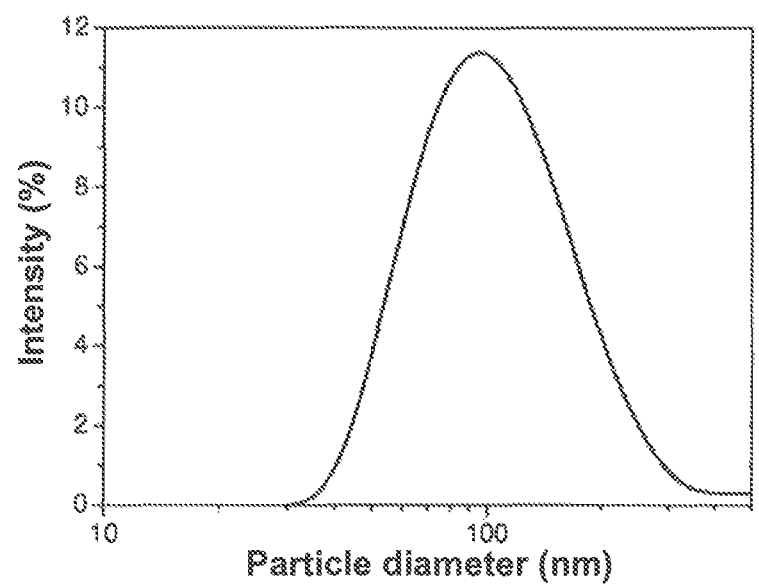
FIG. 2 shows the particle size distribution obtained by the technique of dynamic light scattering to a suspension of calcium carbonate nanoparticles synthesized by process presented in this invention.

The present invention relates to continuous process of producing a high concentration of nanoparticles, wherein all of the particles have sizes less than 1000 nm and are suspended in a non-aggregate form in aqueous phase. In this way, the nanoparticles obtained with the process of the present invention may have particle sizes between 30 nm and 500 nm.

Nanoparticles disclosed in the present invention are formed by a protein matrix in which are embedded primary particles of organic or inorganic nature forming a multicore type nanoparticle, where the protein matrix also is a nanoparticle functionalizing agent. The primary particles of nanoparticle have sizes below 10 nm, that is, between 0.1 nm and 10 nm and its content in the nanoparticles of the present invention is between 50% and 95%, wherein the remaining percentage corresponds to the protein matrix.

The continuous process for producing nanoparticles according to the present invention comprises the following steps a) Provide two different, water soluble precursor solutions of organic or inorganic salts prepared at pH between 6 and 14, and a temperature between 2° C. and 50° C., containing protein and optionally solubilized active ingredient in one or two precursor solutions;

b) Mixing precursor solutions in a quick and continuous way using a high pressure homogenizer having a T-type reactor operating at a pressure between 10 MPa and 400 MPa with temperature control between 2° C. and 95° C.; and c) Receive recently formed nanoparticles in a container that may contain water or aqueous diluents which prevents aggregation of nanoparticles.

In the case of nanoparticles as encapsulating medium, transport or controlled release of chemical or biological compounds, these compounds are added to one or both precursor salt solutions prior to synthesis, adjusting among other parameters pH, conductivity and temperature of precursor solutions.

The salts molar ratio in precursor solutions required for nanoparticles formation of can be in the range between 0.5 and 1.5. These solutions may have one or more proteins and one or more solubilized active principles. Protein or proteins mixture employed as nanoparticles dispersants and stabilizers are solubilized in one or both precursor salt solutions prior to their mixing.

Solutions are mixed on a high pressure homogenization equipment having a T-type reactor, wherein each salt solution or salt precursors is provided in separate compartments of the homogenizer, and then mixing the two high pressure inlet streams converging in a reactor zone to mix instantaneously and flowing in a continuous way out of reactor after generating nanoparticles by applying high pressure to flow conditions that may be in the laminar or turbulent regime, preferably in a turbulent state where the dimensionless Reynolds number, defined as the ratio between shear forces and convective forces, has values between. ten thousand (10,000) and ten million (10,000,000). Required pressures for preparation of nanoparticles can be between 10 MPa and 400 MPa.

In order to produce nanoparticles, the flow conditions in terms of the Reynolds number must generate mixing times on the order of seconds, even better, on the order of milliseconds, wherein these times should be less than the reaction times of the nanoparticle precursor salts. Nanoparticle concentration in final suspension is between 1 and 10 g of nanoparticles for each 100 g of suspension.

To prevent nanoparticles aggregation just after their formation and to the high pressure homogenizer output, may require immediate dilution of nanoparticles suspension depending on the salt concentration used for synthesis.

In the present invention the protein material used for producing nanoparticles has dispersing and stabilizing activity, which allows the formation of the multicore type nanoparticles and confers time stability to nanoparticles, among protein compounds which may he used to prepare Nanoparticles of the present invention include, without excluding others, milk proteins, proteins from meat and vegetables. Mainly proteins that can participate in the process according to the invention and which can act as dispersants, stabilizers and functionalizing agents of nanoparticles, are selected from the group consisting of milk proteins along with their soluble salts such as whey protein, casein, caseinate, beta-lactalbumin, egg protein as ovalbumin, sarcoplasmic and myofibrillar meat proteins and vegetable proteins such as soy protein, corn, rice, barley, canola, oats or mixtures thereof.

Related active ingredients in the present invention may be chemical or biological compounds which may be encapsulated or associated with nanoparticles. In particular, active ingredients such as drugs, pesticides, dyes, aromas, flavorings, and biotechnological products, among others, can be solubilized in one or both phases of the aqueous solutions of precursor salts to be encapsulated within the protein matrix of nanoparticles according to the process of the invention.

Nanoparticles obtained by the producing process encapsulate water-soluble active ingredients, incorporated into the precursor solutions in-situ during nanoparticles formation, with concentrations of active ingredients in the precursor salts of at least 0.01 g to 10 g of active compound per 100 g of saline, and precursor salts concentration are in a range from 50 mM to 5M.

Protein concentration added to solutions of precursor inorganic salts according to the process of the invention is at least 0.1 g to 10 g of proteins per 100 g of salt solution.

According to the content of this invention, functionalized nanoparticles obtained by high pressure continuous process can be used as a food supplement in the case of employing composite precursor salts, for example, calcium or iron, alike can also be used as encapsulating of active ingredients for pharmaceutical or veterinary use, the nanoparticles can also be used as means of transport or controlled release of chemical or biological compounds physically adsorbed on the surface or attached by chemical bonding to the surface, The pH of the system during the process can be adjusted, to values above 6. Increasing the pH to values greater than 10 may cause an increase in the size of the nanoparticles to values above 500 nm.

System temperature can be adjusted to values between 2° C. and 50° C., generating an increase in particle size with increasing temperature.

The precursor salts concentration used in the synthesis is between 50 mM to 5 M. Additionally, the protein material concentration in the initial system to react in the T type reactor, is between 0.1 g and 10 g of protein per 100 g of salt solution, and can be composed of one or more proteinaceous materials, preferably milk proteins with dispersants, stabilizers and functionalizing capabilities. The encapsulated active ingredients in nanoparticles are in concentrations between 0.01 g and 10 g of active ingredient per 100 g of precursor salt solution of nanoparticle synthesis.

EXAMPLES

The invention is further illustrated by the following examples not limiting the scope of the invention.

Example 1

Preparation of calcium carbonate nanoparticles stabilized with sodium caseinate according to the present invention.

A solution of 0.3 M sodium carbonate and 1% sodium caseinate at a pH of 7.0 was prepared and poured into one compartment of high pressure homogenizer, in the same way was prepared a solution of calcium chloride at a concentration of 0.3 M and pH 7.0, which was poured into a second compartment of high pressure homogenizer. Subsequently, the homogenizer pistons was moved at high speed by a pneumatic mechanism to a working pressure of 30 MPa to force the rapid mixing of the solutions of sodium carbonate-sodium caseinate and calcium chloride to produce calcium carbonate nanoparticles functionalized with milk protein, sodium caseinate. Generated nanoparticles had an average size of 170 nm intensity as the technique of dynamic light scattering, and did not settled down after three months, as measured in an automatic tensiometer equipped with accessories to determine sedimentation.

Example 2

Preparation of calcium phosphate nanoparticles stabilized with sodium caseinate according to the present invention.

A solution of 0.2 M sodium acid phosphate and 1% sodium caseinate at a pH of 7.0 was prepared and poured into one of the compartments of the high pressure homogenizer, in the same way was prepared a solution of calcium chloride at a concentration of 0.2 M and pH 7.0 which was poured into a second compartment of the high pressure homogenizer. Subsequently, homogenizer pistons was moved at high speed by a pneumatic mechanism to a working pressure of 30 MPa to force the rapid mixing of solutions of sodium acid phosphate salts and sodium caseinate and calcium chloride thus generate calcium phosphate nanoparticles functionalized with milk protein, sodium caseinate. Generated nanoparticles had an intensity average size of 150 nm accordingly with dynamic light scattering technique and did not settled down after two months as measured in an automatic tensiometer equipped with accessories to determine sedimentation.

Example 3

Preparation of calcium carbonate nanoparticles stabilized with sodium caseinate as encapsulating medium of active ingredients for therapeutic activity.

A solution of 0.1 M sodium carbonate, 1% sodium caseinate and 0.1% quercetin as anticarcinogenic at pH 7.0 was prepared and poured into one of the compartments of the high pressure homogenizer, similarly was prepared a calcium chloride solution at a concentration of 0.1 M and pH 7.0 which was poured into a second compartment of the high pressure homogenizer. Subsequently, homogenizer pistons was moved at high speed by a pneumatic mechanism to a working pressure of 30 MPa to force the rapid mixing of calcium carbonate, sodium caseinate and calcium chloride solutions to produce calcium carbonate nanoparticles functionalized with milk protein with sodium caseinate. Generated nanoparticles had an intensity average size of 190 nm as measured accordingly with dynamic light scattering technique and did not settled down after three months as measured in an automatic tensiometer equipped with accessories to determine sedimentation. Quercetin encapsulation efficiency was 60% measured using UV-Vis spectrophotometry technique.

Figure 3:
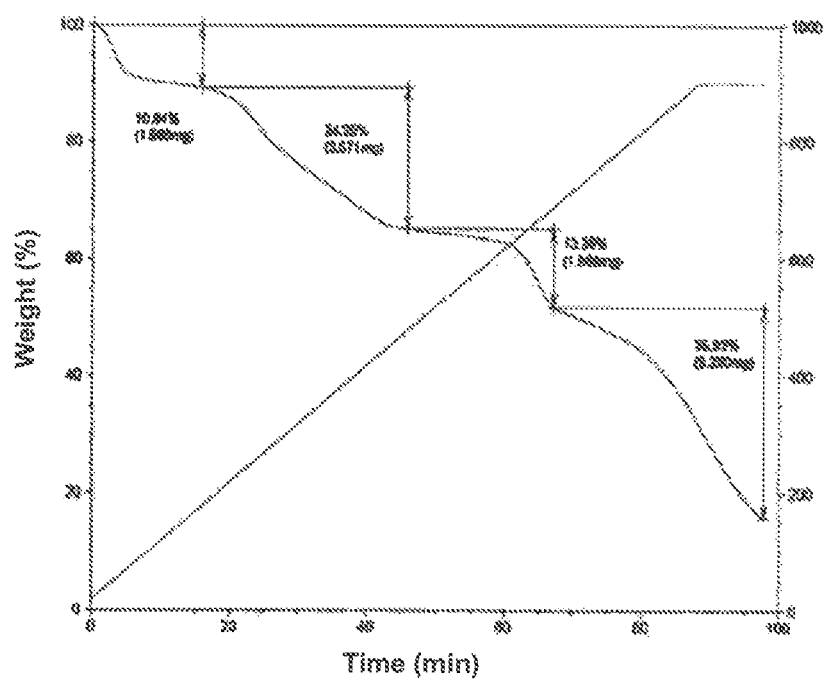
FIG. 3 illustrates the thermal gravimetric analysis of calcium carbonate nanoparticles prepared in accordance with the invention.
Figure 4:
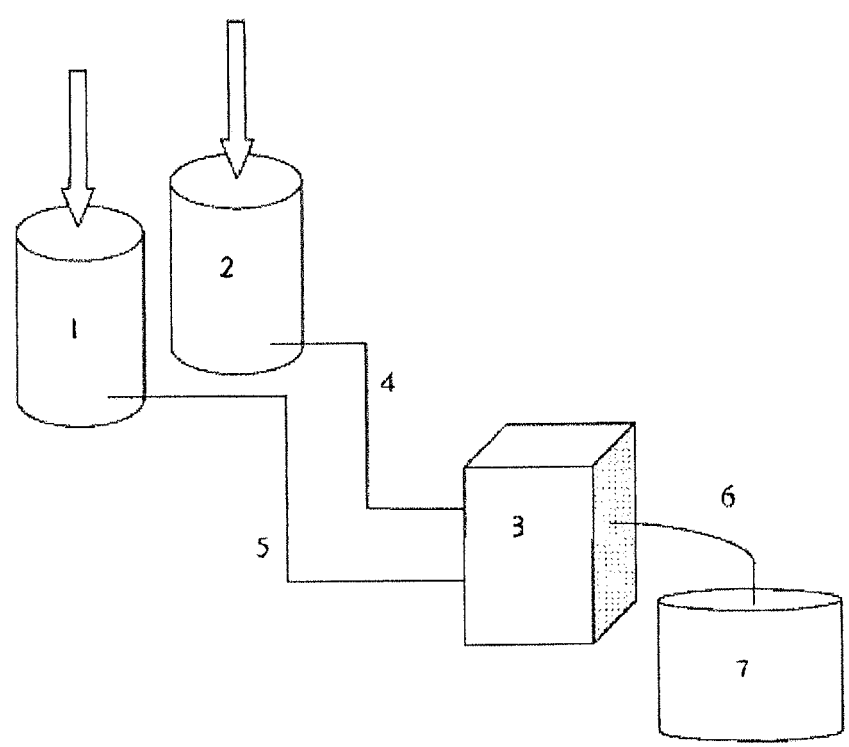
FIG. 4 is a schematic representation of the continuously high pressure homogenizer, used for the preparation of functionalized inorganic nanoparticles according to the invention. In compartments (1) and (2) are poured forming salt solutions that are bring into the mixing chamber (3) through the ducts (4) and (5) and evicted from there by duct (6) to the container (7).

Generated and functionalized nanoparticles with protein material are stable to aggregation and sedimentation for periods up to three months, characteristics evaluated by dynamic light scattering technique, using Doppler effect and by weight gain on a tensiometer, respectively. The particles nanometer size is confirmed by laser light scattering techniques and better yet, by transmission electron microscopy technique, where multicore type nanoparticles was observed with sizes below 500 nm, at primary particle sizes less than 10 nm are embedded in a protein matrix that represents less than 50% by weight of the nanoparticles, as shown in FIG. 1, and according to thermogravimetric analysis which results are illustrated in FIG. 3, where shows a percentage of nanoparticle protein of 35.93% and remaining calcium carbonate.

The invention claimed is:
1. A continuous process for producing nanoparticles comprising the following stages:
    a) providing two different water soluble precursor solutions of organic or inorganic salts prepared at a pH between 6 and 10, and a temperature between 2° C. and 50° C., containing proteins and a solubilized active ingredient in one or two of the precursor solutions;
    b) continuously mixing the precursor solutions using a high pressure homogenizer having a T-type reactor operating at a pressure between 20 MPa and 250 MPa with temperature control between 2° C. and 95° C. to allow the formation of the nanoparticles; and c) receiving the nanoparticles in a container that contains water or aqueous diluents, preventing the nanoparticles from aggregating;

wherein the nanoparticles obtained by the process have particle sizes between 30 to 500 nm;

and wherein the nanoparticles are formed by a protein matrix in which primary particles of organic or inorganic nature are embedded forming multicore-type nanoparticles, and the primary particles represent from 50% to 95% of the nanoparticles, and the remaining percentage corresponds to the protein matrix.

2. The continuous process according to claim 1, wherein the water soluble inorganic precursor salts are selected from the group consisting of magnesium salts, calcium salts, barium salts, strontium salts, carbonates salts, phosphates salts, silicates salts, sulfates salts, oxalates salts, citrates salts, and mixtures thereof.

3. The continuous process according to claim 1 wherein the proteins of step a) are dispersants, stabilizers and functionalizing agents of nanoparticles, and are selected from the groups consisting of:
  i) milk proteins or soluble salts thereof;
  ii) egg protein;
  iii) sarcoplasmic and myofibrillar meat proteins;
  iv) vegetable proteins; and
  mixtures thereof.

4. The continuous process according to claim 1, wherein the concentration of the precursor salts is in the range of 50 mM to 5 M.

5. The continuous process according to claim 1, wherein the amount of the protein added to the precursor solutions of inorganic salts is 0.1 g to 10 g of protein per 100 grams of salt solution.

6. The nanoparticles obtained by the continuous process according to claim 1, characterized in that having sizes between 30 and 500 nm, consisting of primary particles with sizes smaller than 10 nm embedded in a protein matrix, where the primary particles represent from 50% to 95% of the nanoparticles and the remaining percentage corresponding to the protein matrix.

7. The nanoparticles obtained by the continuous process according to claim 1, characterized in that encapsulate or associate water soluble active ingredients incorporated in the precursor solutions in-situ during the formation of nanoparticles, with amounts of active ingredients in the precursor salts at least 0.01 g to 10 g of active ingredient per 100 grams of salt solution.

8. The continuous process according to claim 3, wherein milk proteins are selected from the group consisting of whey protein, caseins, caseinate, beta lactalbumin, and mixtures thereof.

9. The continuous process according to claim 3, wherein the egg protein is ovalbumin.

10. The continuous process according to claim 1, wherein the vegetable proteins are selected from the group consisting of soy protein, corn protein, rice protein, barley protein, canola protein, oats proteins, and mixtures thereof.

* * * * *